US008676305B2

(12) United States Patent
Hayam et al.

(10) Patent No.: US 8,676,305 B2
(45) Date of Patent: Mar. 18, 2014

(54) AUTOMATED ANALYSIS OF COMPLEX FRACTIONATED ELECTROGRAMS

(75) Inventors: Gal Hayam, Tivon (IL); Limor Elran, Haifa (IL); Aharon Turgeman, Zichron Ya'acov (IL); Yaariv Khaykin, Richmond Hill (CA)

(73) Assignee: Biosense Webster (Israel) Ltd., Yokneam (IL)

( * ) Notice: Subject to any disclaimer, the term of this patent is extended or adjusted under 35 U.S.C. 154(b) by 5 days.

(21) Appl. No.: 13/425,512

(22) Filed: Mar. 21, 2012

(65) Prior Publication Data

US 2013/0253349 A1    Sep. 26, 2013

(51) Int. Cl.
*A61B 5/04*    (2006.01)

(52) U.S. Cl.
USPC .......... 600/509; 607/4; 607/5; 607/9; 607/14; 600/510

(58) Field of Classification Search
USPC ........................................ 600/510
See application file for complete search history.

(56) References Cited

U.S. PATENT DOCUMENTS

2007/0197929 A1    8/2007    Porath et al.
2010/0274123 A1    10/2010   Voth

FOREIGN PATENT DOCUMENTS

WO    WO 2007/035306 A2    3/2007

OTHER PUBLICATIONS

Nademanee, K. et al. A New Approach for Catheter Ablation of Atrial Fibrillation: Mapping of the Electrophysiologic Substrate, J. Am. Coll. Cardiol. 2004;43;2044-2053.
European Search Report completed Jun. 21, 2013 for corresponding Patent Application No. EP13166191.
Koonlawee, N., et al., "A New Approach for Catheter Ablation of Atrial Fibrillation: Mapping of the Electrophysiologic Substrate", Journal of the American College of Cardiology, vol. 43, No. 11, pp. 2044-2053 Jun. 2, 2004). XP002578066.
Takahashi, et al., "Characterization of Electrograms Associated with Termination of Chronic Atrial Fibrillation by Catheter Ablation", Journal of the American College of Cardiology, vol. 51, No. 10 (Mar. 4, 2008). XP022510750.

*Primary Examiner* — Michael Kahelin
*Assistant Examiner* — Mallika D Fairchild
(74) *Attorney, Agent, or Firm* — Louis J. Capezzuto (57)    ABSTRACT

A method for mapping abnormal electrical activity, including obtaining electrical signal data from respective locations in a heart of a living subject, and automatically analyzing the signal data to identify complex fractionated electrograms (CFEs) therein. The method further includes analyzing the CFEs so as to identify reentry locations comprised in the respective locations, and displaying information derived from the identification in relation to a map of the heart.

9 Claims, 5 Drawing Sheets

AUTOMATED ANALYSIS OF COMPLEX FRACTIONATED ELECTROGRAMS

FIELD OF THE INVENTION

The present invention relates generally to electrocardiography, and specifically to automatic analysis of electrocardiograms.

BACKGROUND OF THE INVENTION

In the document *A New Approach for Catheter Ablation of Atrial Fibrillation: Mapping of the Electrophysiologic Substrate*, Nademanee et al., J. Am. Coll. Cardiol., 2004; 43(11): 2044-2053, which is incorporated herein by reference, it is proposed that atrial fibrillation may be successfully treated by ablating sites exhibiting a complex fractionated atrial electrogram (CFAE). The authors identified areas of CFAE during atrial fibrillation, and then applied radiofrequency ablation to these areas. As a result of the ablation, the atrial fibrillation was resolved in the large majority of the cases.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method for mapping abnormal electrical activity, including:

obtaining electrical signal data from respective locations in a heart of a living subject;

automatically analyzing the signal data to identify complex fractionated electrograms (CFEs) therein;

analyzing the CFEs so as to identify reentry locations comprised in the respective locations; and displaying information derived from the identification in relation to a map of the heart.

Typically the CFEs include complex fractionated atrial electrograms (CFAEs).

In a disclosed embodiment identifying the reentry locations includes assigning a window of interest (WOI) to a given CFE, and identifying qualifying deflections within the WOI, the qualifying deflections consisting of peaks lying between predefined minimum and maximum voltages. The method may further include evaluating a number of the qualifying deflections (NODs), and identifying the reentry locations includes verifying that the number lies within a predefined range of numerical values. Typically, evaluating the number includes adjusting the number to account for noise in the qualifying deflections.

The disclosed embodiment may further include:

identifying a first qualifying deflection and a last qualifying deflection;

measuring a total fractionation time (TFT) period between the first and the last qualifying deflections; and verifying that the TFT period lies within a predefined range of periods of time.

There is further provided, according to an embodiment of the present invention, apparatus for mapping abnormal electrical activity, including:

a probe which is configured to receive electrical signal data from respective locations in a heart of a living subject; and a processor which is configured:

to automatically analyze the signal data to identify complex fractionated electrograms (CFEs) therein, to analyze the CFEs so as to identify reentry locations included in the respective locations, and to display information derived from the identification in relation to a map of the heart.

There is further provided, according to an embodiment of the present invention, a computer software product for mapping electrical activity, including a tangible computer-readable medium in which computer program instructions are stored, which instructions, when read by a computer, cause the computer to:

receive electrical signal data from respective locations in a heart of a living subject;

automatically analyze the signal data to identify complex fractionated electrograms (CFEs) therein;

analyze the CFEs so as to identify reentry locations comprised in the respective locations; and display information derived from the identification in relation to a map of the heart.

The present disclosure will be more fully understood from the following detailed description of the embodiments thereof, taken together with the drawings, in which:

DETAILED DESCRIPTION OF EMBODIMENTS

OVERVIEW

In an embodiment of the present invention a processor automatically analyzes electrograms from respective regions of a heart, typically a human heart, in order to identify regions generating complex fractionated electrograms (CFEs). The electrograms are typically, although not necessarily derived from regions in an atrium of the heart, in which case the electrograms are complex fractionated atrial electrograms (CFAEs).

The processor further automatically analyzes the identified CFEs to delineate qualifying deflections in a predefined period, a window of interest (WOI), of the electrogram, and to enumerate the qualifying deflections as a number of deflections (NOD). A qualifying deflection comprises a turning point of the signal, i.e., a local maximum or a local minimum of the signal, which lies between predefined maximum and minimum voltage bounds. In addition to delineating qualifying deflections, the processor also automatically analyzes the qualifying deflections to determine a total fractionation time (TFT) between the first and the last qualifying deflections.

Typically, the processor incorporates the values of NODs of the respective regions into a map of the heart that is displayed to a medical professional performing a procedure on the heart. Alternatively or additionally, a map of TFT values may be incorporated into the map.

The medical professional may provide the processor with predefined ranges of values of NODs and TFTs that define regions of reentry in the heart. The processor is able to incorporate the predefined ranges into a display of the maps described above. From the display, professional is able to identify the regions of reentry and typically ablates the regions to remove the reentry. A similar analysis to that described above may be used to determine if reentry is no longer occurring in the ablated regions.

System Description

Figure 1:
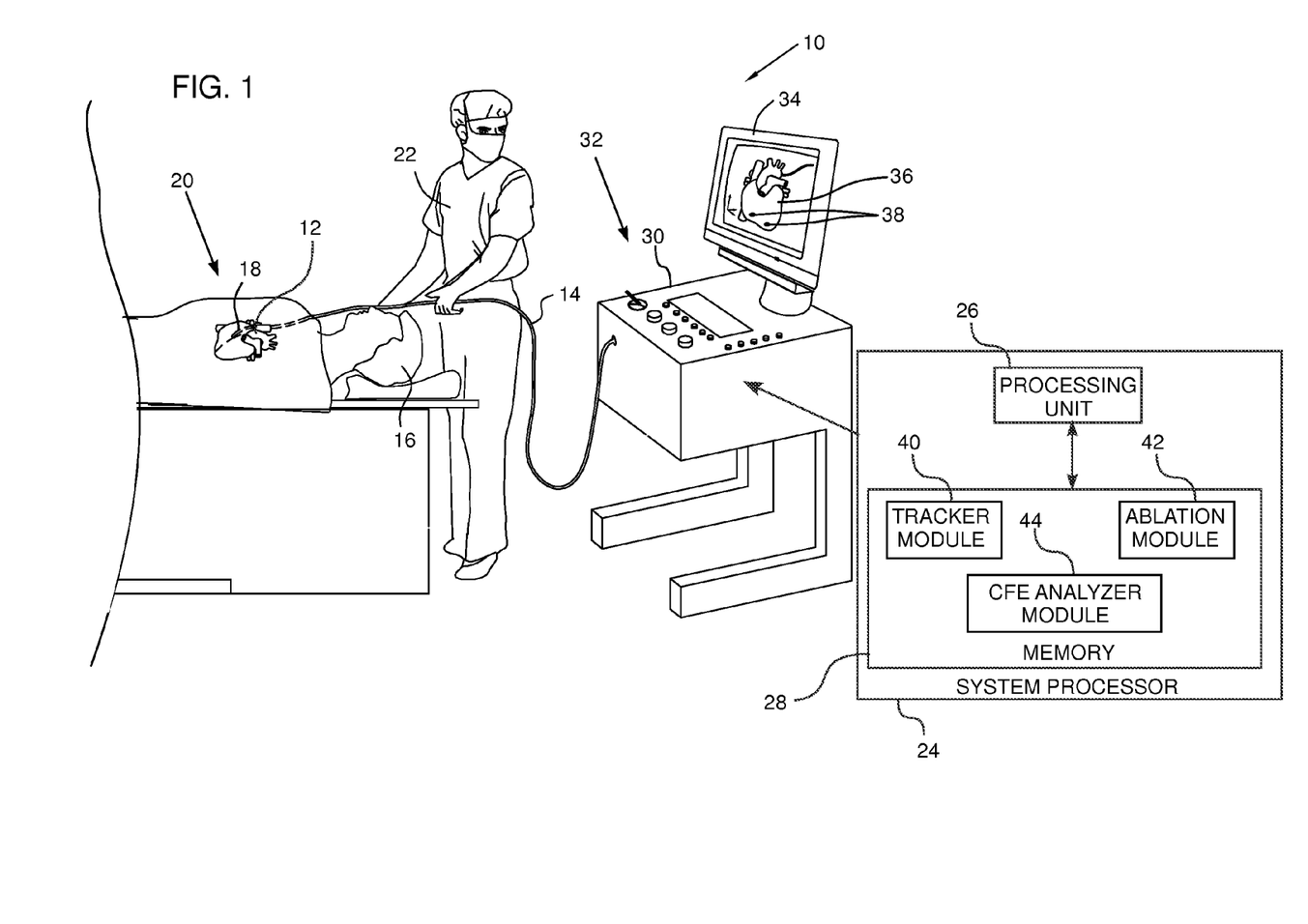
FIG. 1 is a schematic illustration of an electrogram analysis system, according to an embodiment of the present invention.

Reference is now made to FIG. 1, which is a schematic illustration of an electrogram analysis system 10, according to an embodiment of the present invention. For simplicity and clarity, the following description, except where otherwise stated, assumes an investigative procedure wherein system 10 performs measurements on a heart 12, herein assumed to comprise a human heart, using a probe 14. As well as having facilities for performing electrogram analysis, system 10 typically also includes facilities for tracking probe 14, as well as for ablating one or more regions of heart 12. The following description assumes that these latter facilities are present in system 10, and that they are available for use during the investigative procedure.

Typically, probe 14 comprises a catheter which is inserted into the body of a subject 16 during an investigative procedure. A distal tip 18 of the probe comprises an electrode 20 which receives electrocardiograph (ECG) signals from the heart of the subject, and the signals are analyzed by system 10, as described herein. The investigative procedure is performed by a user 22 of system 10, and in the description herein user 22 is assumed, by way of example, to be a medical professional.

Typically other electrodes may be used during the procedure. The other electrodes may be attached to probe 14, to another probe similar to probe 14 and located within the heart, and/or to the skin of subject 16. The other electrodes may be used as reference electrodes, for example to give a reference for the timing of signals from electrode 20, and/or to provide a reference ground for the signals from electrode 20 (in which case the signals are unipolar signals). Alternatively or additionally at least one of the other electrodes may be used for determining a voltage differential with electrode 20, in which case the signals generated by electrode 20 are bipolar signals. For simplicity, other electrodes used during the procedure are not illustrated in FIG. 1, but are assumed to be present in system 10 as required.

System 10 is typically controlled by a system processor 24 which may be realized as a general purpose computer. The system processor comprises a processing unit 26 communicating with a memory 28. Processor 24 may be mounted in a console 30, comprising operating controls 32 that typically include a keypad and a pointing device such as a mouse or trackball that professional 22 uses to interact with the processor. Results of the operations performed by processor 24 are provided to the professional on a screen 34 which displays a diagram 36 of the results of the analysis performed by the system. The screen typically displays other items 38 of auxiliary information related to the heart while the heart is being investigated, such as the positions of distal tip 18, and the positions of other catheters used by professional 22. Screen 34 typically also presents a graphic user interface to the professional. Professional 22 is able to use controls 32 to input values of parameters used by processor 24 in the operation of system 10.

Processor 24 uses computer software, including a probe tracker module 40, an ablation module 42, and a complex fractionated electrogram (CFE) analyzer module 44 stored in memory 28, to operate system 10. The software may be downloaded to processor 24 in electronic form, over a network, for example, or it may, alternatively or additionally, be provided and/or stored on non-transitory tangible computer-readable media, such as magnetic, optical, or electronic memory.

Probe tracker module 40 tracks sections of probe 14 while the probe is within subject 16. The tracker module typically tracks both the location and orientation of the distal tip of the probe, within the heart of subject 16. In some embodiments module 40 tracks other sections of the probe. The tracker module may use any method for tracking probes known in the art. For example, module 40 may operate magnetic field transmitters in the vicinity of the subject, so that magnetic fields from the transmitters interact with tracking coils located in sections of the probe being tracked. The coils interacting with the magnetic fields generate signals which are transmitted to the module, and the module analyzes the signals to determine a location and orientation of the coils. (For simplicity such coils and transmitters are not shown in FIG. 1.) The Carto® system produced by Biosense Webster, of Diamond Bar, Calif., uses such a tracking method. Alternatively or additionally, tracker module 40 may track the distal tip of probe 14 by measuring impedances between electrode 20 and electrodes on the skin of subject 16. (In this case electrode 20 may be used for both ECG detection and tracking.) The Carto3® system produced by Biosense Webster uses both magnetic field transmitters and impedance measurements for tracking.

Using tracker module 40 processor 24 is able to measure locations of distal tip 18, and form location coordinates of the locations for use in diagram 36.

Ablation module 42 allows professional 22 to use system 10 for ablating tissue in heart 12. The ablation module typically applies the ablation by providing radiofrequency (RF) energy to electrode 20, or to another electrode on tip 18. Such an RF ablation system is well known in the art, and is available in the Carto® systems referenced above. (In some cases electrode 20 may be used for ablation, as well as providing both ECG and tracking signals.) Alternatively, ablation module 42 may implement any other form of tissue ablation known in the art, such as ultrasonic or cryogenic ablation.

In the document A *New Approach for Catheter Ablation of Atrial Fibrillation: Mapping of the Electrophysiologic Substrate*, Nademanee et al., referenced above, it is proposed that atrial fibrillation may be successfully treated by ablating sites exhibiting a complex fractionated atrial electrogram (CFAE). CFAEs may be defined as atrial electrograms that have fractionated electrograms composed of two deflections or more, and/or perturbation of the baseline with a continuous deflection of a prolonged activation complex over a 10 s recording period; or as atrial electrograms with a very short cycle length (e.g., 120 ms) averaged over a 10 s recording period. The recording period is not critical, and recording intervals of other lengths may be used.

Principles of the present invention may be applied to complex fractionated electrograms (CFEs) from all heart chambers, not just to CFAEs. In addition, the principles can be applied for epicardial as well as for endocardial approaches, and to mapping in sinus rhythm, as well as when many different cardiac arrhythmias are present.

Electrogram analyzer module 44 analyzes the ECG signals received from electrode 20 to determine if the signals can be classified as complex fractionated electrograms (CFEs). The processing of ECG signals to make such a determination is generally as explained in US Patent Application 2007/0197929, to Porath et al., which is incorporated herein by reference.

Initially analog signal data from electrode 20 is automatically processed, typically using an analog to digital converter, and conditioned, typically by applying filtration. The resultant signal is analyzed to identify voltage maxima or minima, herein also termed voltage peaks, having amplitudes within a predefined voltage range. The analysis continues by identifying peak-to-peak time intervals between the identified voltage peaks that occur within a predefined time range. The analyzed results are then applied, using a definition of a CFE provided below with reference to the flowchart of FIG. 3, to determine if the electrogram may be classified as a CFE. Each identified CFE corresponds to a respective area within heart 12, and the locations of the areas can be measured using tracker module 40.

Module 44 further analyzes and characterizes the CFEs to identify areas of the heart that may contain reentry. While the further analysis and characterization of the electrograms may be performed off-line, the inventors have found that it can also be performed in real time on-line.

The analysis performed using module 44 is described in more detail below with respect to the flowchart of FIG. 3.

Figure 2:
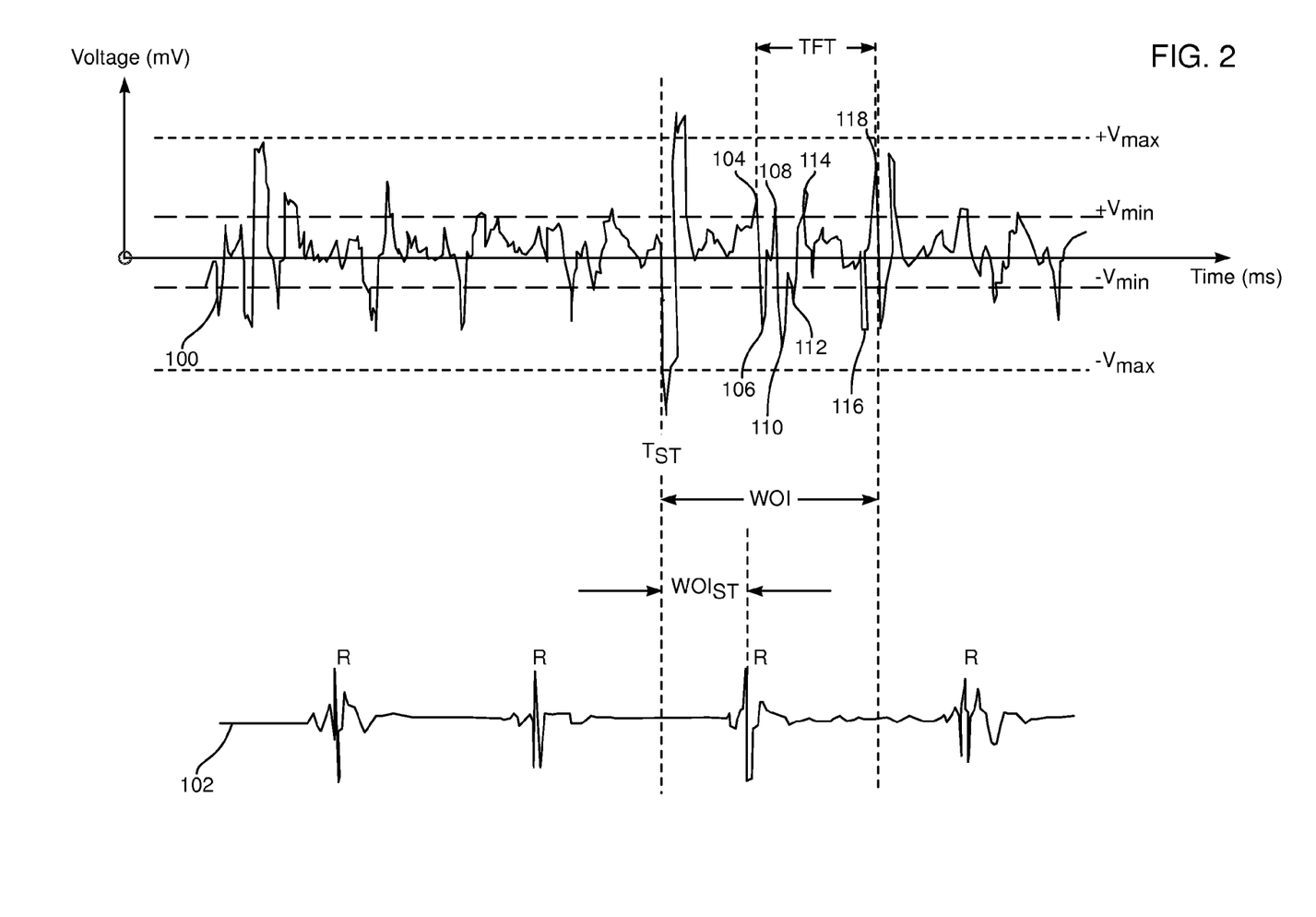
FIG. 2 shows schematic graphs of electrograms generated by an analyzer module of the system, according to an embodiment of the present invention.

FIG. 2 shows schematic graphs of electrograms generated by module 44, according to an embodiment of the present invention. A graph 100 is a first bipolar electrogram generated by electrode 20 together with another electrode used as a reference. Graph 100 is produced when electrode 20 is in contact with a given area of one of the heart atria. A graph 102 is a second bipolar electrogram, generated at the same time as graph 100, between two reference electrodes. Parameters and other elements of the graphs are explained in Table I below, and also in the description of the flowchart of FIG. 3.

Figure 3:
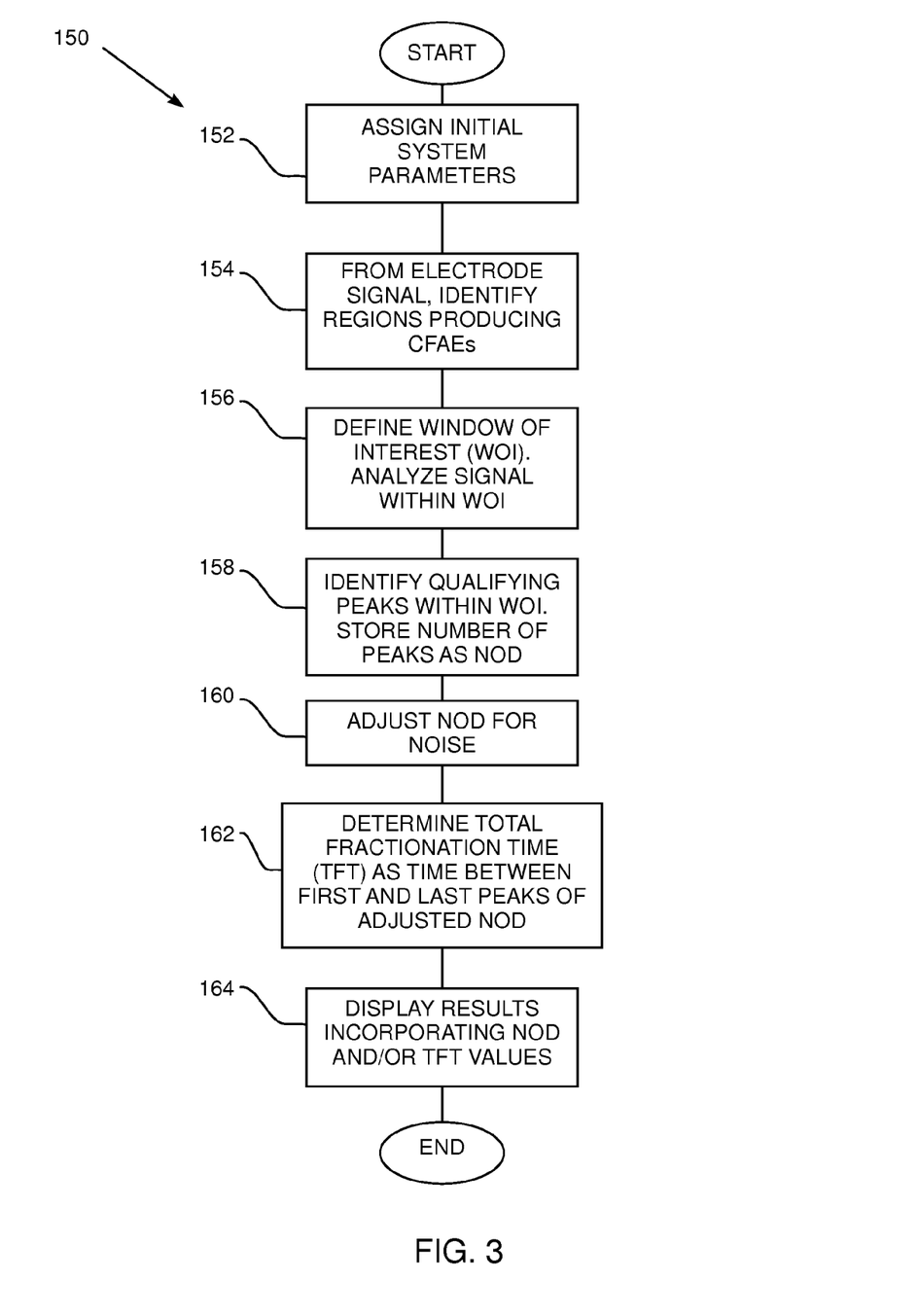
FIG. 3 is a flowchart of steps followed by a processor using the analyzer module, according to an embodiment of the present invention.

FIG. 3 is a flowchart 150 of steps followed by processor 24, using analyzer 44, according to an embodiment of the present invention. The following description of the steps assumes that an electrogram is generated from electrode 20 contacting a region of one of the atria, and for clarity assumes that graph 100 (FIG. 2) corresponds to a portion of the electrogram.

In an initial setup step 152, professional 22 assigns values for parameters that are to be used by the processor and analyzer 44 in analyzing a signal from electrode 20. Parameters and typical user-defined values of the parameters that may be assigned in this step are shown in Table I. (The remarks in the Table are further explained in the description of the steps of the flowchart.)

TABLE I

| Parameter | Typical/Nominal Value | Remarks |
|---|---|---|
| Minimum Positive Threshold $+V_{min}$ | +0.05 mV | Voltage bounds for positive qualifying peak |
| Maximum Positive Threshold $+V_{max}$ | +0.15 mV | |
| Minimum Negative Threshold $-V_{min}$ | −0.05 mV | Voltage bounds for negative qualifying peak |
| Maximum Negative Threshold $-V_{max}$ | −0.15 mV | |
| Minimum Duration $T_{min}$ | 50 ms | Time bounds for qualifying interval |
| Maximum Duration $T_{max}$ | 120 ms | |

TABLE I-continued

| Parameter | Typical/Nominal Value | Remarks |
|---|---|---|
| Voltage Threshold $V_{th}$ | 0.03 mV | Voltage and tim values used in analyzing a complex |
| Duration Threshold $T_{th}$ | 50 ms | |
| Window of Interest time period WOI | 800 ms | Nominal value, typically determined by R-R period |
| WOI start time period $WOI_{ST}$ | 400 ms | Nominal value. The time period before the first R peak, indicating time instant $T_{ST}$ where the WOI starts |

In a CFE identification step 154, processor 24 identifies regions of heart 12 which produce CFEs. The identification is generally as described in US Patent Application 2007/0197929 referenced above, and involves initial analysis of an electrogram from the region using the parameters as described in step 152 and Table I. For clarity, the initial analysis is assumed to be performed on an electrogram that is obtained over a 10 s period of time, but, as stated above, the period could be longer or shorter. The analysis is performed on each cycle of the beating heart comprised in the electrogram, a cycle typically being the time period between consecutive R peaks from a reference signal received by reference electrodes, such as is illustrated in graph 102 (FIG. 2).

The CFE identification step comprises the processor using analyzer 44 to delineate qualifying peaks during each cycle from electrode 20. A qualifying peak has a turning point having its maximum between $+V_{min}$ and $+V_{max}$. Such a qualifying peak, having a positive voltage value, is also termed a positive qualifying peak. Alternatively, a qualifying peak has a turning point having its minimum between $-V_{min}$ and $-V_{max}$, and such a qualifying peak, having a negative voltage value, is also termed a negative qualifying peak. The identification also comprises measuring time intervals between the peaks and enumerating as qualifying intervals those intervals which lie within times bounded by the minimum and maximum durations, $T_{min}$ and $T_{max}$.

A typical region assumed to have a CFE has four or more qualifying intervals, the presence of the number of qualifying intervals defining a CFE. However, the number of qualifying intervals used to determine if a region has a CFE may be selected to be more or less than this number, according to a degree of confidence required by professional 22. The higher the number of qualifying intervals, the greater the degree of confidence that the electrogram comprises a CFE.

In a first analysis step 156, for each given region having a CFE, analyzer 44 considers the signal data within a window of interest (WOI). The WOI may be a user-defined time period, and is herein assumed by way of example to be the period in time of one cycle, as defined above. The WOI is applied to the signal from a start time $T_{ST}$ of the WOI defined by a start time period $WOI_{ST}$. The start time is typically a time instant that is midway between adjacent R peaks. However, as for the WOI itself, the start time $T_{ST}$ of the WOI may be user-defined.

In an initial deflection enumeration step 158, the processor identifies qualifying peaks, also herein termed qualifying deflections, within the WOI. As shown in FIG. 2, there is a group of eight qualifying deflections: 104, 106, 108, 110, 112, 114, 116, and 118. Of these, deflections 104, 108, 114, and 118 are positive qualifying peaks, and deflections 106, 110, 112, and 116 are negative qualifying peaks. The processor stores the number of deflections (NOD), i.e., the total number of identified positive and negative qualifying peaks, in memory 28.

In an adjustment step 160, the processor adjusts for peaks that may have been caused by noise, using values of the voltage and duration thresholds, $V_{th}$ and $T_{th}$, defined in setup step 152. The processor analyzes positive peaks and negative peaks separately. Two positive qualifying peaks are assumed to be separate, so that the two peaks are counted within NOD as two separate peaks, if there is a minimum voltage difference between the two peaks of $V_{th}$ and if there is a minimum time difference between the two peaks of $T_{th}$. If both conditions are not met, then the two peaks are counted as one in NOD. The processor applies similar conditions to decide if two negative qualifying peaks are assumed to be separate.

For example, assume the values of $V_{th}$ and $T_{th}$ are the typical values shown in Table I, that peak 110 has a voltage −0.12 mV, that peak 112 has a voltage −0.06 mV, and that the separation time between the peaks is 30 ms. In this case even though the two peaks are separated by more than $V_{th}$, they are counted as one peak since their separation time is less than $T_{th}$, and the adjusted value of NOD becomes seven, in place of the "raw" NOD value determined in step 158.

In a fractionation time step 162, the processor quantifies the time period, in milliseconds, between the first and last peaks in the group of peaks comprising the NOD. The time period is termed the total fractionation time (TFT) of the electrogram. FIG. 2 illustrates that the TFT of graph 100 is the time (in ms) between peak 104 and peak 118.

In a results step 164, values of the NOD assigned to each CFE region, or values of the TFT assigned to each CFE region, are displayed to professional 22. The display is typically graphical, but may alternatively or additionally be numerical. Examples of the display in a graphical format are shown in FIGS. 4 and 5.

Figure 4:
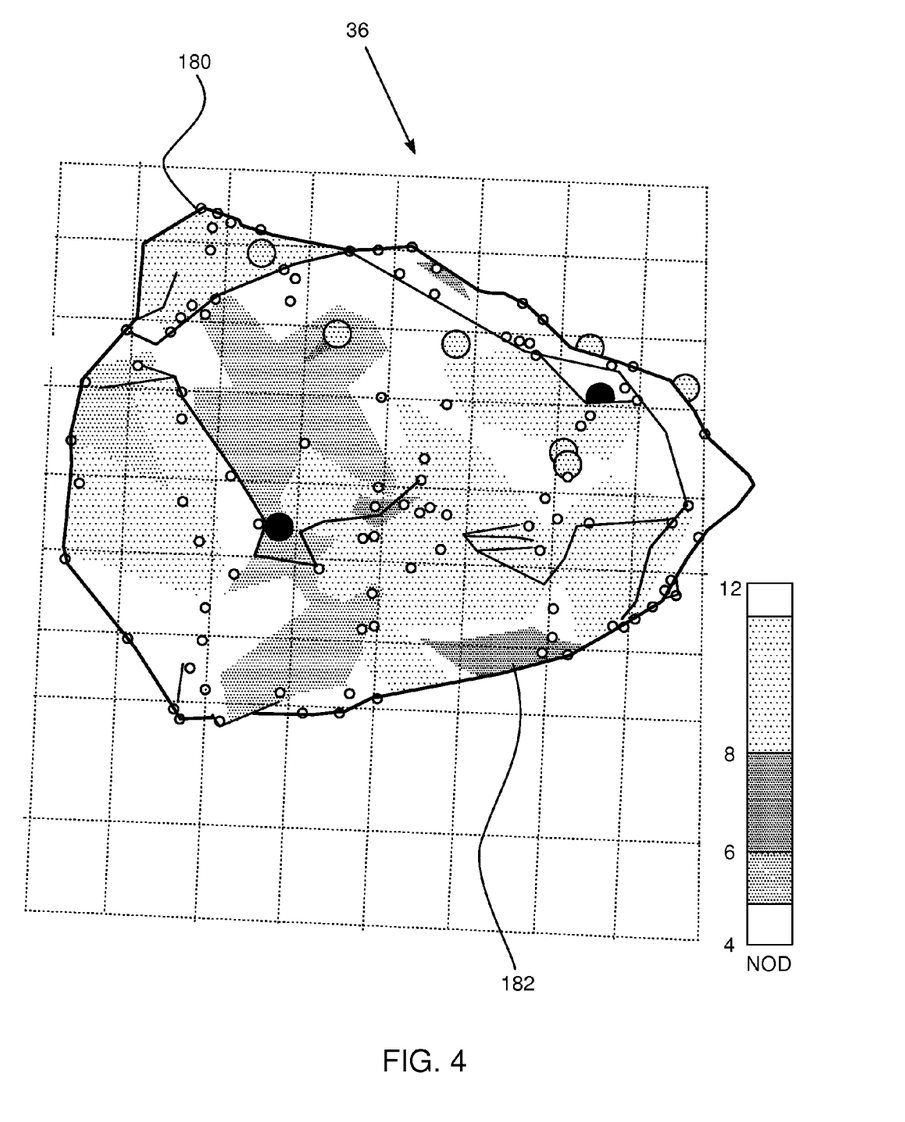
FIG. 4 is a schematic illustration depicting a section of a heart, according to an embodiment of the present invention.

FIG. 4 is a schematic illustration of diagram 36 (FIG. 1) depicting a section 180 of heart 12, showing values of NOD mapped according to their respective spatial locations, according to an embodiment of the present invention. The NOD values are color coded according to a color scale, and the appropriate colors are incorporated into a map of section 180. Alternatively or additionally, the NOD values may be displayed numerically. The values of NOD are assumed, by way of example, to have an overall range from 4 to 12. Professional 22 typically chooses a set of values of NOD that identifies and verifies potential reentry sites based on the professional's experience, as well as on other factors such as historical NOD data. For example, the professional may select sites having NOD values between 6 and 8 as being potential reentry sites, in which case a region 182 is one such site, and is typically a candidate for ablation.

It will be understood that the above presented overall range of NOD values and the potential reentry site NOD values are by way of example, and the scope of the present invention includes other overall NOD ranges and potential reentry site NOD values that will be apparent to those having ordinary skill in the art.

Figure 5:
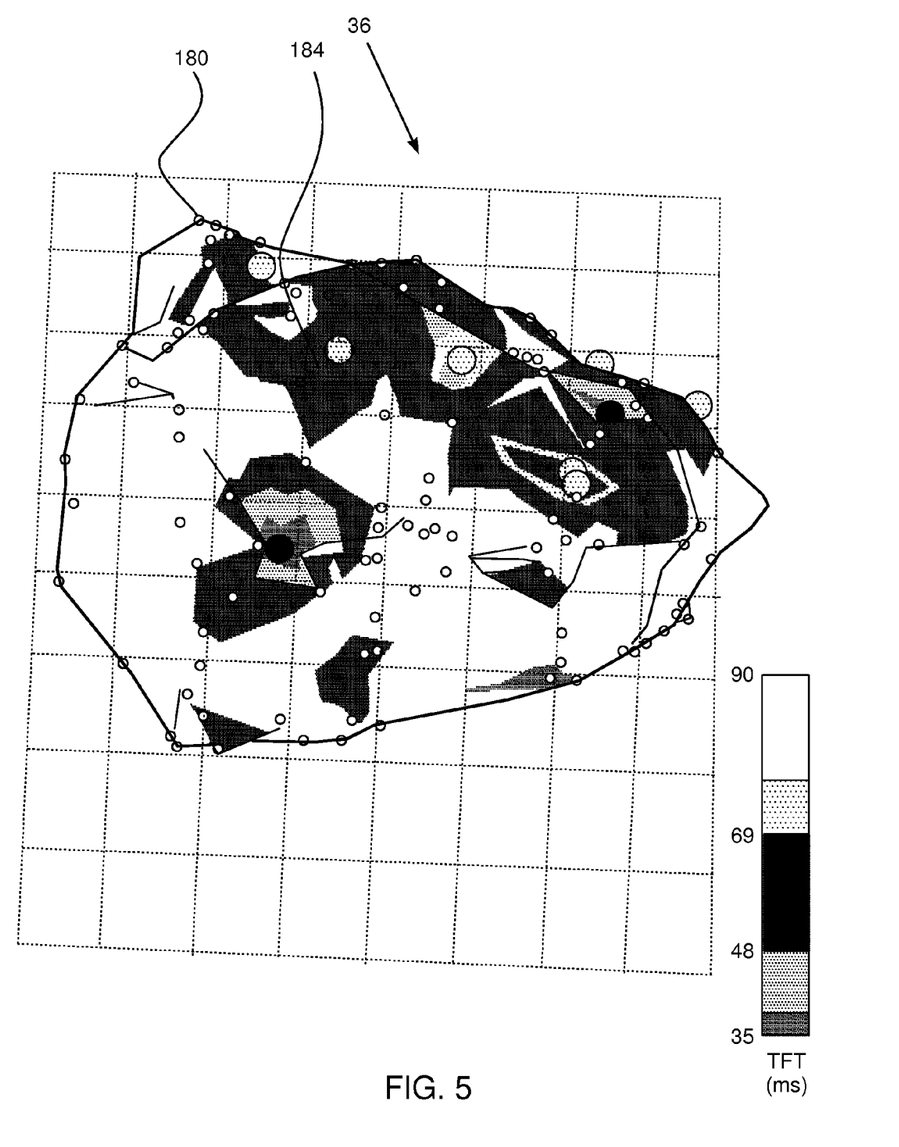
FIG. 5 is a schematic illustration depicting the section, according to an alternative embodiment of the present invention.

FIG. 5 is a schematic illustration of diagram 36 depicting section 180, showing values of TFT mapped according to their respective locations in heart 12, according to an embodiment of the present invention. The TFT values are color coded according to a color scale, and the appropriate colors are incorporated into a map of section 180. Alternatively or additionally, the TFT values may be displayed numerically.

The values of TFT are assumed, by way of example, to have an overall range from 35 ms to 90 ms. Professional typically chooses a set of values of TFT that identifies and verifies potential reentry sites in a similar manner to the method used for choosing values for NOD. As an example, the professional may select sites having TFT values between 48 ms and 69 ms as being potential reentry sites, in which case a region 184 is a reentry site. As for the NOD values, the above presented overall range of TFT values and the potential reentry site TFT values are by way of example, and the scope of the present invention includes other overall TFT ranges and potential reentry site TFT values that will be apparent to those having ordinary skill in the art.

Typically, professional 22 is able to switch the display on screen 34, so as to view the map of NOD values or the map of TFT values. Using one or both maps, the professional typically uses tracker module 40 and ablation module 42 to ablate the reentry sites indicated by one or both of the maps. Once the ablation has been performed, professional 22 is able to use system 10 to verify that sites which qualified as reentry sites, according to the NOD or TFT criteria given above, no longer qualify as reentry sites using the same criteria. Typically the ablated sites do not exhibit complex fractionated behavior.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for mapping abnormal electrical activity, comprising:
   obtaining electrical signal data from respective locations in a heart of a living subject;
   automatically analyzing the signal data to identify complex fractionated electrograms (CFEs) therein;
   analyzing the CFEs so as to identify reentry locations comprised in the respective locations;
   establishing predefined minimum and maximum voltages $V_{th}$ and a predefined duration threshold $T_{th}$;
   assigning a window of interest (WOI) to a given CFE, and identifying qualifying deflections within the WOI, the qualifying deflections comprising peaks lying between predefined minimum and maximum voltages $V_{th}$ and evaluating a number of the qualifying deflections (NODs);
   adjusting for noise by verifying that the NODs lie within both the predefined minimum and maximum voltages $V_{th}$ and the predefined duration threshold $T_{th}$ and adjusting the NODs to account for noise when both the predefined minimum and maximum voltages $V_{th}$ and the predefined duration threshold $T_{th}$ conditions are not met; and
   displaying information derived from the identification in relation to a map of the heart.

2. The method according to claim 1, wherein the CFEs comprise complex fractionated atrial electrograms (CFAEs).

3. The method according to claim 1, and comprising:
   identifying a first qualifying deflection and a last qualifying deflection;
   measuring a total fractionation time (TFT) period between the first and the last qualifying deflections; and
   verifying that the TFT period lies within a predefined range of periods of time.

4. Apparatus for mapping abnormal electrical activity, comprising:
- a probe which is configured to receive electrical signal data from respective locations in a heart of a living subject; and
- a processor which is configured:
- to automatically analyze the signal data to identify complex fractionated electrograms (CFEs) therein,
- to analyze the CFEs so as to identify reentry locations comprised in the respective locations by: (i) establishing predefined minimum and maximum voltages $V_{th}$ and a predefined duration threshold $T_{th}$; (ii) assigning a window of interest (WOI) to a given CFE, and identifying qualifying deflections within the WOI, the qualifying deflections comprising peaks lying between predefined minimum and maximum voltages $V_{th}$ and evaluating a number of the qualifying deflections (NODs); (iii) adjusting for noise by verifying that the NODs lie within both the predefined minimum and maximum voltages $V_{th}$ and the predefined duration threshold $T_{th}$ and adjusting the NODs to account for noise when both the predefined minimum and maximum voltages $V_{th}$ and the predefined duration threshold $T_{th}$ conditions are not met, and
- to display information derived from the identification in relation to a map of the heart.

5. The apparatus according to claim 4, wherein the CFEs comprise complex fractionated atrial electrograms (CFAEs).

6. The apparatus according to claim 4, wherein the processor is further configured:
- to identify a first qualifying deflection and a last qualifying deflection,
- to measure a total fractionation time (TFT) period between the first and the last qualifying deflections, and
- to verify that the TFT period lies within a predefined range of periods of time.

7. A computer software product for mapping electrical activity, including a tangible non-transitory computer-readable medium in which computer program instructions are stored, which instructions, when read by a computer, cause the computer to:
- receive electrical signal data from respective locations in a heart of a living subject;
- automatically analyze the signal data to identify complex fractionated electrograms (CFEs) therein;
- analyze the CFEs so as to identify reentry locations comprised in the respective locations by: (i) establishing predefined minimum and maximum voltages $V_{th}$ and a predefined duration threshold $T_{th}$; (ii) assigning a window of interest (WOI) to a given CFE, and identifying qualifying deflections within the WOI, the qualifying deflections comprising peaks lying between predefined minimum and maximum voltages $V_{th}$ and evaluating a number of the qualifying deflections (NODs); (iii) adjusting for noise by verifying that the NODs lie within both the predefined minimum and maximum voltages $V_{th}$ and the predefined duration threshold $T_{th}$ and adjusting the NODs to account for noise when both the predefined minimum and maximum voltages $V_{th}$ and the predefined duration threshold $T_{th}$ conditions are not met; and
- display information derived from the identification in relation to a map of the heart.

8. The product according to claim 7, wherein the CFEs comprise complex fractionated atrial electrograms (CFAEs).

9. The product according to claim 7, and comprising: causing the computer to:
- identify a first qualifying deflection and a last qualifying deflection;
- measure a total fractionation time (TFT) period between the first and the last qualifying deflections; and
- verify that the TFT period lies within a predefined range of periods of time.

* * * * *